United States Patent
Sutton et al.

(10) Patent No.: US 11,832,994 B2
(45) Date of Patent: Dec. 5, 2023

(54) ULTRASOUND CONTROL UNIT

(71) Applicant: KONINKLIJKE PHILIPS N.V., Eindhoven (NL)

(72) Inventors: Jonathan Thomas Sutton, Boston, MA (US); Alexander Groth, Hamburg (DE); Frank Michael Weber, Hamburg (DE); Shyam Bharat, Arlington, MA (US); Peter Bingley, Mierlo (NL); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 291 days.

(21) Appl. No.: 17/288,028

(22) PCT Filed: Oct. 21, 2019

(86) PCT No.: PCT/EP2019/078470
§ 371 (c)(1),
(2) Date: Apr. 23, 2021

(87) PCT Pub. No.: WO2020/083795
PCT Pub. Date: Apr. 30, 2020

(65) Prior Publication Data
US 2021/0378638 A1 Dec. 9, 2021

Related U.S. Application Data

(60) Provisional application No. 62/750,332, filed on Oct. 25, 2018.

(30) Foreign Application Priority Data

Nov. 6, 2018 (EP) ..................................... 18204584

(51) Int. Cl.
*A61B 8/00* (2006.01)
*A61B 8/08* (2006.01)

(52) U.S. Cl.
CPC ................ *A61B 8/546* (2013.01); *A61B 8/54* (2013.01); *A61B 8/56* (2013.01); *A61B 8/58* (2013.01); *A61B 8/585* (2013.01); *A61B 8/5223* (2013.01)

(58) Field of Classification Search
CPC .... A61B 8/54; A61B 8/56; A61B 8/58; A61B 8/585
See application file for complete search history.

(56) References Cited

U.S. PATENT DOCUMENTS 5,509,413 A  4/1996  Akama
5,997,479 A  12/1999  Savord
(Continued)

FOREIGN PATENT DOCUMENTS

WO  2006054259 A1  5/2006
WO  2015130070 A2  9/2015

OTHER PUBLICATIONS

International Search Report and Written Opinion of PCT/EP2019/078470, dated Nov. 13, 2019.

*Primary Examiner* — Colin T. Sakamoto (57) ABSTRACT

An ultrasound control unit (10) is for coupling with an ultrasound transducer unit (12). The control unit is adapted to control a drive configuration or setting of the transducers of the transducer unit, each drive setting having a known power consumption level associated with it. The control unit includes a control module (20) adapted to adjust the drive setting from a first setting to a second setting, the second having a lower associated power consumption that the first. The second setting is tested by an analysis module (16), the analysis module adapted to determine a measure of reliability of ultrasound data acquired by the transducer unit, for the
(Continued)

purpose of deriving at least one physiological parameter, when configured in the second setting. The second setting is only used if its determined reliability passes a pre-defined reliability condition.

16 Claims, 3 Drawing Sheets

(56) References Cited

U.S. PATENT DOCUMENTS

| | | |
|---|---|---|
| 6,013,032 A | 1/2000 | Savord |
| 6,283,919 B1 | 9/2001 | Roundhill |
| 6,443,896 B1 | 9/2002 | Detmer |
| 6,458,083 B1 | 10/2002 | Jago |
| 6,530,885 B1 | 3/2003 | Entrekin |
| 6,542,846 B1 | 4/2003 | Miller |
| 6,623,432 B2 | 9/2003 | Powers |
| 7,559,899 B2 | 7/2009 | Lo |
| 8,439,842 B2 | 5/2013 | Kabakov |
| 8,600,299 B2 | 12/2013 | Randall |
| 2003/0158479 A1 | 8/2003 | Li |
| 2003/0163045 A1 | 8/2003 | Gatzke |
| 2008/0114247 A1 | 5/2008 | Urbano |
| 2012/0020187 A1 | 1/2012 | Kunita et al. |
| 2017/0128020 A1 | 5/2017 | Oliver et al. |

ULTRASOUND CONTROL UNIT

CROSS-REFERENCE TO PRIOR APPLICATIONS

This application is the U.S. National Phase application under 35 U.S.C. § 371 of International Application No. PCT/EP2019/078470, filed on Oct. 21, 2019, which claims the benefit of U.S. Provisional Patent Application Ser. No. 62/750,332, filed Oct. 25, 2018 and European Patent Application No. 18204584.9, filed on Nov. 6, 2018. These applications are hereby incorporated by reference herein.

FIELD OF THE INVENTION

This invention relates to an ultrasound control unit for controlling an ultrasound transducer unit, and in particular for managing a drive setting of the transducer unit.

BACKGROUND OF THE INVENTION

Ultrasound imaging is a widespread modality used to diagnose various cardiac conditions.

Recent advancements in image processing algorithms and transducer development have enabled continuous monitoring applications. Many new clinical insights can be gained from continuous monitoring as compared to a single scan. It also offers benefits over other monitoring techniques due to its non-invasiveness, absence of risk of infection, and absence of any ionizing radiation.

Ultrasound acquisition may be coupled with intelligent image analysis and signal processing algorithms for example. Such systems are becoming a valuable tool for patient monitoring at the point-of-care.

One particularly valuable application for continuous ultrasound monitoring may be cardiac hemodynamic monitoring, since it offers the potential to monitor cardiac dynamics in real time and noninvasively. It offers a viable alternative to the use of a pulmonary artery catheter, an invasive device that provides periodic measurements of cardiac output and ventricular pressure measurements. The latter is becoming increasingly unpopular with clinicians due to its invasive nature.

Monitoring enables for instance the monitoring of certain physiological or anatomical parameters, connected for instance with hemodynamics, such as cardiac output, ventricular size or volume, or other blood flow parameters.

Conventional ultrasound imaging solutions are not designed for long term monitoring. A common problem is overheating of the ultrasound transducer when operated for the extended periods required for continuous monitoring.

Overheating causes conventional ultrasound devices either to fail or to automatically enter cool-down cycles to limit probe or tissue heating. During this period, no data can be collected.

Ultrasound, when used in long-term monitoring mode requires continuous operation throughout the monitoring period. Intermittent shut-down periods are not clinically acceptable.

Further to this, in some applications, such as mobile systems, available power is in general limited, for example if an ultrasound transducer unit is battery powered or supplied by low-power sources such as a USB output. Continuous monitoring in these cases quickly drains available power, or even overloads the limited power supply.

An improved approach to ultrasound monitoring is required to enable continuous monitoring over extended periods without overheating, while at the same time not limiting accuracy of acquired data or of monitored physiological parameters.

SUMMARY OF THE INVENTION

The invention is defined by the claims.

According to examples in accordance with an aspect of the invention, there is provided an ultrasound control unit, operably coupleable with an ultrasound transducer unit, the control unit comprising:

an acquisition module operable to control acquisition of ultrasound data using the ultrasound transducer unit, and further operable to configure a drive setting of the ultrasound transducer unit, each possible drive setting have an associated transducer power level known or derivable by the acquisition module;

a data analysis module operable to perform a testing procedure based on acquired ultrasound data, to determine a measure of reliability of the data for deriving one or more physiological parameters, and to determine whether said reliability measure meets a defined reliability condition; and a control module adapted, using the acquisition module and the data analysis module, to adjust a drive setting of the transducer unit from a first setting to a second, lower power, setting, wherein the second setting meets said pre-defined reliability condition applied by the data analysis module.

The invention is based on reconfiguring a drive setting of the transducer unit to a new setting which has a lower associated power consumption. By lowering power consumption, problems of overheating can be ameliorated. Lower power drive settings may typically encompass less intensive or less expansive data collection, and hence data resolution or breadth or detail may be reduced.

To avoid deteriorating quality or resolution of data too far, the unit includes the functionality to test a level of reliability of collected data, at a particular drive setting mode, to determine its suitability or sufficiency for use in determining one or more physiological parameters of interest. The new, lower power, setting is switched to on an ongoing or final basis only in the case that the result of this reliability test meets some defined minimum reliability condition.

The control unit may hence be for optimizing drive settings of a transducer unit for the purpose of monitoring or measuring or more physiological parameters.

Embodiments of the invention are hence based on reducing acoustic power of the ultrasound system in a manner that does not preclude accurate variable quantification over long durations. By inclusion of a reliability testing procedure, power output can be reduced, enabling ultrasound imaging over long periods, while still retaining robust parameter quantification based on derived images.

For the purpose of the present disclosure, ultrasound data may for example refer to raw echo signal data, e.g. RF data, received from a transducer or transducer array of the transducer unit. It may alternatively for example refer to data which has been post-processed in some way. The data may include signal data, for instance echo signal data, or may include numerical or tabular, or image data for example.

The power level referred to above may mean a power consumption level, e. g. power consumption associated with the setting.

Each drive setting may correspond to a configuration of a set of one or more acquisition parameters of the ultrasound transducer unit, i.e. each drive setting may encompass settings for a set of acquisition parameters. These may include, by way of non-limiting example, transmit voltage, line density, beam widths, 2D vs 3D acquisition mode, field of view size, frame rate, pulse duration, settings related to a window function of the pulse, and/or settings related to transmit or receive aperture apodization.

A drive setting of the transducer unit may more generally encompass a configuration of a set of one or more operating parameters of the transducer unit, connected with various aspects of the acoustic output of the transducer unit. These may include for instance parameters associated with a transmit voltage of transducers in the transducer unit, parameters associated with the intensity or shape of ultrasound beams generated by the transducer unit, and/or parameters associated with a transmit frequency or acquisition frame rate.

The invention is not limited to any particular drive settings or group of drive settings, and the inventive concept may be applied to any settings related to acoustic or driving operation of the transducer unit for instance. In some examples for instance, the control unit may comprise means for permitting a user or operator to define custom drive settings (having associated power levels) and with the control unit configured to utilize these custom defined drive settings in the drive setting adjustment procedure.

The testing procedure comprises determining a measure of reliability of data for deriving one or more physiological parameters. This may mean a measure of reliability of the data for the purpose of deriving one or more physiological parameter measurements based on this data, or based on an image or images derived from the data for instance. Physiological parameter measurements may include anatomical measurements, e.g. dimensions of one or more anatomical bodies or features for instance.

The measure of reliability may be quantitative, or may alternatively be binary for instance. It may in some examples comprise a measure of similarity with previously acquired data or pre-stored reference data.

The second drive setting may advantageously be selected to be a minimum available power level setting which meets the pre-defined reliability condition. The control unit may hence implement a step of selecting the second drive setting, this selection being based on minimizing power level, subject to the constraint of meeting the pre-defined reliability condition.

There may in some cases be a set of available drive settings, each with a known or derived associated power level, this set being known to the control unit. The control unit may select as the second drive setting the setting which has the lowest power level which meets the pre-defined reliability condition. This may for example involve acquiring sample ultrasound data in each of a plurality of available drive settings for instance, in incrementing power levels, until one is found which meets the reliability condition for instance.

The lowest power setting may be identified and selected through a step-wise or iterative adjustment procedure, as discussed below.

The testing procedure implemented by the data analysis module may be based on reference to previously acquired, or pre-stored, ultrasound data or information derived therefrom.

For purposes of the present disclosure, information derived from ultrasound data refers to any information, data, measurement, or result deriving from the ultrasound data. It may include for instance a physiological parameter measurement derived from the data. It may include one or more images derived from the data. It may include one or more physiological parameter measurements derived from one or more images, where the images are derived from the acquired ultrasound data.

The testing procedure may be based on direct comparison with the previously acquired or pre-stored data or information, or it may be based on comparison of a secondary factor or variable associated with the prior data or information. For instance, the testing procedure may be based on first determining a deviation of the acquired data from some standard dataset, and a deviation of a set of previously acquired or pre-stored data, from some standard dataset, and then the reliability measure determined based on level of similarity between those two derived deviation measures.

Previously acquired data may be previously acquired data representative of substantially the same anatomical region or feature.

The previously acquired data may be or include previously acquired data in a different power level setting. The previously acquired data may include data previously acquired in each of a plurality of different power level settings. The previously acquired data may include subsets of data acquired at different time points, or across different time intervals.

In advantageous examples, the previously acquired data may be data acquired during the same imaging session as the data the being tested or analyzed. In this way it can be better ensured that the derived average measure of similarity being used as a reference is representative of the current anatomical situation or scenario for instance. However, this is not essential, and other examples may differ.

Pre-stored data may include reference data or standard data for example. The control unit may include a memory. The pre-stored data may be pre-stored in this memory.

The measure of reliability may be based on a determined measure of similarity of acquired ultrasound data, or information derived therefrom, with said previously acquired, or pre-stored, data, or information derived therefrom.

The reliability condition may be an imposed minimum similarity threshold, or a maximum deviation threshold for instance, i.e. where data should meet a minimum level of similarity with previously acquired data.

The measure of reliability may in some examples be based at least on a similarity of acquired ultrasound data, or information derived therefrom, of the second drive setting with corresponding data or information derived therefrom of the first drive setting.

The measure of reliability may be based on a measure of similarity with previously acquired data, or information derived therefrom, the previously acquired data having been acquired within a defined time period of the data being tested.

The reliability condition may be a minimum threshold for said measure of similarity.

By ensuring that comparison is made with data collected within some threshold preceding time period, it is better ensured that the previous data is representative of substantially the same anatomical picture or situation as the data being tested. This means that any deviation between the two sets of data, or information derived therefrom, can be assumed to be substantially due to loss of quality or accuracy or reliability of the acquired data.

In one or more alternative examples, the measure of similarity may be based on determining a measure of deviation of data from pre-stored or reference data, and the reliability condition comprising a minimum threshold for similarity of said deviation with deviations of previously acquired data from said pre-stored or reference data.

According to any of the above examples, the minimum similarity threshold may be set based on a pre-stored or derived average measure of similarity between previously acquired, or pre-stored, data subsets, or information derived therefrom. Said previous data subsets may be data subsets acquired within a defined time period of one another.

Here, the required minimum similarity threshold is set based on reference to a typical or average fluctuation between data when acquired in the past. Where large fluctuation between different data points or subsets is normal, the allowable deviation between newly acquired data and previously acquired data may be set to be larger, i.e. the similarity threshold set smaller. If typical fluctuation is small, the minimum required similarity threshold may be set larger.

In preferred examples, the derived average measure of similarity may be between previously acquired data acquired within in the same imaging session as the data being tested or analyzed. In this way, it can be better ensured that the derived average measure of similarity being used as a reference is representative of the current anatomical situation or scenario for instance. An imaging session may be understood as a period during which image data is being acquired for a given patient on a particular occasion.

According to one or more examples, the testing procedure may be based on deriving one or more ultrasound images from acquired ultrasound data and wherein the measure of reliability is based on a similarity of one or more characteristics of the derived image(s) with corresponding characteristics of image(s) derived from previously acquired or pre-stored ultrasound data.

According to an advantageous set of embodiments, the adjustment of the drive setting may be performed as a stepwise adjustment between the first and second settings, comprising stepping through successive drive setting steps of differing power levels.

Stepwise may mean iterative. A step-wise adjustment may comprise moving to the second setting in (a series of) steps, where at each new setting step an assessment is made as to whether the best setting has yet been found. The best setting might for example mean the lowest power drive setting which continues to meet the reliability condition.

The step-wise adjustment may reach the second setting immediately, in which case there are no intermediate steps. More usually, the step-wise adjustment will involve a series of intermediate setting steps between the first setting and the second setting.

At least a portion of the successive drive setting steps may have successively lower associated power levels.

All of the successive drive settings may have successively lower drive settings in some examples.

In other examples for instance a first portion of the successive drive settings may have successively lower drive settings, while one or more subsequent drive settings may have a successively higher drive setting. For instance, where it is detected that the reliability condition is no longer met by a successive drive setting, a successively next drive setting may be chosen with a successively higher power level, and the testing procedure repeated. This represents just one non-limiting example.

Sample ultrasound data may be acquired in each successive drive setting, and a reliability of the sample data tested by the data analysis module.

The step-wise adjustment may be continued until a drive setting is reached which fails to meet said pre-defined reliability condition. The second drive setting may for instance then be selected as the last successive step to meet the pre-defined reliability condition, e.g. the penultimate step in the successive series of steps.

In the case where the successive steps have successively lower associated power levels, this achieves the result that the selected (second) drive setting is the lowest available power level setting which meets the pre-defined reliability condition. This represents just one example. Other examples will be described in further detail in the section to follow.

According to one or more examples, sample ultrasound data may be acquired in each successive drive setting step, and a reliability of the sample data tested by the data analysis module.

The measure of reliability of each successive drive setting in this case may be based on a determined measure of similarity of acquired ultrasound data, or information derived therefrom, with data or information derived therefrom of one or more preceding setting steps.

The reliability condition may comprise a minimum threshold for said measure of similarity for example.

According to certain examples, the measure of reliability may be based on a similarity only with data or measurements of the immediately preceding setting.

It may be advantageous in examples that sample data acquired in each successive step capture essentially the same anatomical picture, i.e. that there is some minimum equivalence of anatomy between each step. This better ensures fair comparison between sample data. For this purpose, according to one or more examples, a relatively high step rate may be implemented.

According to one or more examples, sample ultrasound data may be acquired in each successive drive setting step, and wherein the steps are advanced through at a step rate of at least 1 step per second, for instance at least 10 steps per second. In some examples, the step rate may be at least 20 steps per second, for instance at least 50 steps per second.

This may mean an equivalent or effective step rate. For example, for a step rate of 50 steps per second, if only 10 steps are advanced through, then this would be completed in a maximum of 0.2 seconds.

Each drive setting may encompass a configuration for a set of acquisition parameters, the acquisition parameters including one or more of: transmit voltage, line density, beam widths, 2D vs 3D acquisition mode, field of view size, and/or frame rate.

These represent examples only, and the skilled person will be aware of other acquisition parameters utilized in controlling an ultrasound transducer unit. Acquisition parameters relate in general both to direct power settings of the transducer unit, as well as aspects of an imaging mode, such as 3D imaging or 2D imaging, and also for example selection of a field of view size.

According to an advantageous set of embodiments, the control unit may be further configured to automatically switch to a pre-defined high power drive setting in the event a pre-defined override condition is met. The override condition may optionally be based on properties of acquired ultrasound data and/or inputs of one or more external sensors or devices operatively coupled to the system.

This feature provides an override mode, in which a defined high-power setting is switched to. This allows the efficient power management of the main invention to be also optimally balanced with common instances of requiring high quality, and hence high power imaging. For instance, the high-power setting may be triggered in response to certain threshold levels for one or more vital signs, these indicating a need for more precise measurements, to monitor patient progression in more detail.

Other input factors which may trigger the override setting may include: detected movement of the ultrasound transducer unit relative to the subject body, detected presence of a caregiver (e.g. with a movement or proximity sensor, or through detecting touch of a control panel for instance), detection of one or more physiological conditions which may normally trigger an alarm on a patient monitor, detection of a certain interval of time elapsing.

Examples in accordance with a further aspect of the invention provide an ultrasound system, comprising: an ultrasound transducer unit operable to acquire ultrasound data; and an ultrasound control unit in accordance with any of the examples or embodiments described above or below, or in accordance with any claim of this application, operatively coupled with the ultrasound transducer unit.

Examples in accordance with a further aspect of the invention provide a patient monitoring system comprising:
 a patient monitoring unit; and
 an ultrasound control unit in accordance with any of the examples or embodiments described above or below, or in accordance with any claim of this application.

The patient monitoring unit may for example be coupleable or coupled with one or more physiological parameter (e.g. vital sign) measurement or monitoring devices. The patient monitoring unit may include a display.

The ultrasound transducer unit may comprising one or more ultrasonic transducers, for example one or more transducer arrays. The transducer unit may be any device or unit or element comprising at least one ultrasound transducer having a configurable drive setting, the drive setting for instance corresponding to a configuration of one or more acquisition parameters of the transducer(s). Acquisition parameters has the meaning discussed above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound control unit for coupling with an ultrasound transducer unit. The control unit is adapted to control a drive configuration or setting of the transducers of the transducer unit, each drive setting having a known power consumption level associated with it. The control unit includes a control module adapted to adjust the drive setting from a first setting to a second setting, the second having a lower associated power consumption that the first. The second setting is tested by an analysis module, the analysis module adapted to determine a measure of reliability of ultrasound data acquired by the transducer unit, for the purpose of deriving at least one physiological parameter, when configured in the second setting. The second setting is only used if its determined reliability passes a pre-defined reliability condition.

Embodiments of the invention permit efficient power management of a transducer unit by actively adjusting drive settings to reduce power consumption, while maintaining accuracy of derived physiological parameters being monitored using the transducer unit.

This allows for instance long-term or continuous monitoring of physiological parameters using data collected by a transducer unit without over-heating of transducers of the transducer unit.

Embodiments of the invention are based on adjusting a drive setting of a transducer unit to reduce power consumption. A drive setting of the transducer unit may encompass a configuration of a set of operating parameters of the transducer unit, connected with various aspects of the acoustic output of the transducer unit. These may include for instance parameters associated with a transmit voltage of transducers in the transducer unit, parameters associated with the intensity or shape of ultrasound beam generated by the transducer unit, and/or parameters associated with a transmit frequency or acquisition frame rate.

For simplicity, the set of parameters encompassed by a given drive setting will be referred to in the present disclosure simply as operating parameters or acquisition parameters.

Numerous different operating parameters of the transducer unit affect the time-averaged acoustic power deposited into tissue. Each of these parameters may be individually adjusted during monitoring with ultrasound to achieve an optimal balance between update rate, physiological parameter quantification accuracy, and measurement duration.

By way of example, there will now be outlined a set of example acquisition parameters for a transducer unit, configurations of one or more of which may be encompassed within a given drive setting of the transducer unit according to embodiments of the invention.

One example parameter is transmit voltage, meaning the excitation or drive voltage provided to the transducer element(s) of the transducer unit. Adjusting the transmit voltage may result in lower or higher acoustic intensity of generated vibrations. To reduce power, the transmit voltage may be lowered, resulting in a lower signal-to-noise ratio across the image space.

A further parameter is line density, meaning the angular or lateral density of transmitted ultrasound beams (in B-mode imaging for example). Ultrasound beams may be fired at sparser angles to reduce power consumption, at the cost of reduced lateral resolution of images.

A further parameter is beam width, meaning the lateral or angular width of the ultrasound beams. For example, the focal gain of the ultrasound aperture may be adjusted (e.g. in response to changes in line density) in order to acquire information over a broader volume.

A further parameter is the imaging planes which are captured according to certain modes. For example, instead of acquiring a complete 3D volume, a subset of image data can be gathered at specific relevant locations within the cardiac volume (e.g. informed by live image-segmentation data). This reduces necessary demands on the acoustic transducer unit, thereby reducing the power output. One example of this approach may include for instance using Philips x-Plane which allows capturing two different planes simultaneously through projection of orthogonally crossed planes of beams.

A further parameter is the particular field-of-view (FOV) of the transducer unit. The height and width of the imaging field of view can be adjusted to adjust power output. In particular, the FOV size can be reduced by keeping the same line density but reducing the total number of projected lines. This reduces the total power consumption.

For example, the width and height of a 3D imaging volume may be reduced to only specific restricted anatomical areas (e.g. informed by live segmentation data), dependent on the parameter being monitored.

A further parameter is frame rate, meaning the temporal rate at which ultrasound data is acquired. This may be reduced to thereby limit the time averaged acoustic power, at the expense of the update rate of the monitored physiological parameter(s).

Apparent update rate could be maintained in such examples, by interpolating physiological parameter measurements for missing intermediate time points, though at the cost of accuracy/precision of the parameters. For example, for cardiac related hemodynamic parameters, ultrasound data might be acquired only at end-diastole and end-systole time points, and the resulting measurements used to estimate parameters derived from other phases of the cardiac cycle.

Figure 1:
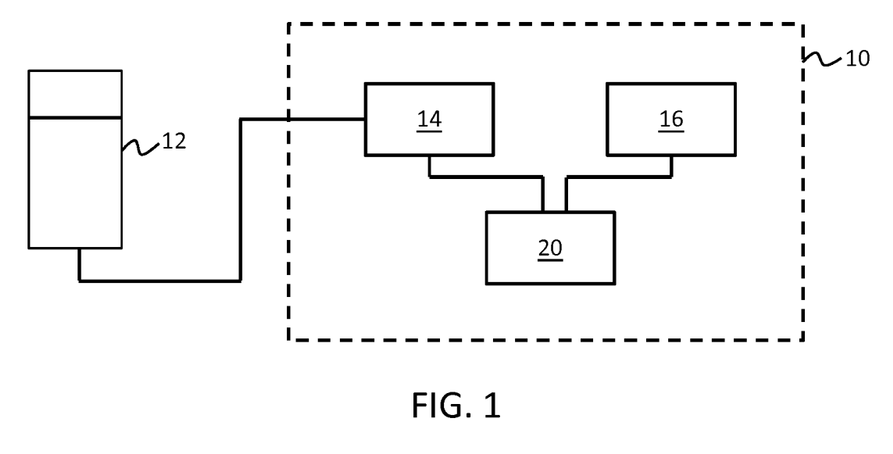
FIG. 1 shows an example ultrasound control unit according to one or more embodiments of the invention, the control unit operatively coupled with an ultrasound transducer unit.

An example ultrasound control unit 10 in accordance with one or more embodiments is shown in block diagram form in FIG. 1. The control unit is adapted to be operably coupleable with an ultrasound transducer unit 12, for example an ultrasound probe, for controlling the transducer unit. An example ultrasound transducer unit 12 is shown operably coupled to an acquisition module 14 of the ultrasound control unit 10 for illustration.

The ultrasound control unit 10 comprises an acquisition module 14 operable to control acquisition of ultrasound data using the ultrasound transducer unit 12, and further operable to control a drive setting of the ultrasound transducer unit, each possible drive setting have an associated transducer power level known or derivable by the acquisition module.

The ultrasound control unit 10 further comprises a data analysis module 16 operable to perform a testing procedure based on acquired ultrasound data, to determine a measure of reliability of the data for deriving one or more physiological parameters, and to determine whether said reliability measure meets a defined reliability condition.

The ultrasound control unit 10 further comprises a control module 18 adapted, using the acquisition module 14 and the data analysis module 16, to adjust a drive setting of the transducer unit 12 from a first setting to a second, lower power level, setting, wherein the second setting meets said pre-defined reliability condition applied by the data analysis module.

Although in FIG. 1 the acquisition module 14, data analysis module 16 and control module 18 are shown as separate elements or components within the control unit 10, this is only by way of illustration. In some examples, the functionality of the different modules may be integrated and performed by a single element, for example by a single controller or processor, or their functionalities may be otherwise distributed between one or more elements or components. Alternatively, the functionality of each module may be performed by a separate controller or processor within the ultrasound control unit.

The ultrasound control unit may include at least one memory, for storing different possible drive setting for the transducer unit, and their associated power levels. This memory may be arranged such that its content is accessible by at least the acquisition module 14.

According to advantageous embodiments, the control unit 10 may be configured to minimize a power output while maintaining the minimum reliability condition of acquired data satisfied.

For example, the second drive setting may be selected to be a minimum available power level setting which meets the pre-defined reliability condition.

The process of adjustment implemented by the control unit 10 may include in some examples at least one step of selecting a candidate lower-power drive setting for adjusting the transducer unit and at least a further step of testing the candidate setting for its reliability for determining one or more physiological parameters of interest. If the derived reliability does not meet the pre-determined reliability condition, the transducer unit 12 is not switched to the tested drive setting on an ongoing or final basis.

There are different approaches both for the process of testing reliability of data acquired in a given drive setting and that of selecting an optimum candidate new drive setting for the transducer unit.

The different possible approaches for testing the reliability of data acquired in a given drive setting for determining a given physiological parameter will be first be discussed. A number of different example approaches will be outlined.

In general, the testing procedure performed by the analysis module is based on assessing the ability of a given ultrasound dataset, or given image derived from that data, or given physiological parameter derived from the data or image to quantify certain anatomical parameters using algorithms known-in-the-art.

According to one group of embodiments, the testing procedure is based generally on reference to previously acquired, or pre-stored, ultrasound data or information derived therefrom. The data analysis module may be adapted to access or retrieve such data or information derived therefrom and to perform the testing procedure at least in part based on reference to this data.

The testing procedure may be based on direct comparison with the previously acquired or pre-stored data or information, or it may be based on comparison of a secondary factor or variable associated with the prior data or information.

In one set of examples for instance, the analysis module may be adapted to access previously acquired ultrasound data (e.g. previously acquired by the acquisition unit, for example stored in a local or remote memory), wherein said data was used for determining the particular physiological parameter of interest, and is assumed or known to have been sufficiently reliable for that purpose. A comparison test may then be performed between the newly acquired data being tested by the analysis module and the previously acquired data, and a measure of similarity derived.

Preferably, the previously acquired data may be data acquired within some threshold time period of acquisition of the new data being tested. In this way, it can be better assumed that the two sets of data represent substantially the same anatomical picture. Hence the majority of any deviation between the two can be attributed to loss of reliability or accuracy or precision of the acquired data.

The reliability condition required by the analysis module may be a minimum threshold for said derived measure of similarity with the previously acquired data. If the newly acquired data is within the minimum similarity threshold, then it satisfies the reliability condition in this example.

The minimum similarity threshold may be set based on a pre-stored or derived average measure of similarity between previously acquired, or pre-stored, data subsets, or information derived therefrom.

The previous data subsets may be data subsets also acquired within the same defined time period of one another.

Here, the required minimum similarity threshold with previously acquired is set based on reference to a typical or average fluctuation between subsets of data when acquired in the past. Where large fluctuation between different data points or subsets is normal, the allowable deviation between newly acquired data and previously acquired data may be set to be larger, i.e. the similarity threshold set smaller. If typical fluctuation is small, the minimum required similarity threshold may be set larger.

The previously acquired data may include for instance subsets of data acquired at different time points, or across different time intervals. A typical or average deviation between data of these subsets may be derived for the purpose of setting the similarity threshold.

The previously acquired data may be or include previously acquired data in a different power level setting. The previously acquired data may include data previously acquired in each of a plurality of different power level settings.

The same comparison procedure as described above may be performed in variant examples with respect to some pre-stored data, e.g. pre-stored in a local or remote memory, where that pre-stored data is also assumed or known to be reliable for determining the particular physiological parameter of interest. Pre-stored data may include reference data or standard data for example.

In a further set of examples, the testing procedure may be based on reference both to previously acquired ultrasound data and to pre-stored ultrasound data. The procedure may comprise first determining a deviation of the newly acquired data from data of a pre-stored or standard dataset. The procedure may then comprise determining a deviation of previously acquired data with the same pre-stored or standard data. The measure of reliability may then be determined based on a level of similarity between those two derived deviation measures. The condition may be a minimum threshold for the similarity between the deviation measures.

This approach is based on using the deviation of the previously acquired data with the pre-stored data as a standard measure of known reliability against which change of the newly acquired data can be compared and assessed. Where the deviation of the newly acquired data from the pre-stored data has increased by a level exceeding an allowable threshold, this is an indication that the newly acquired data is no longer reliable for determining the particular physiological parameter of interest.

As in the previous set of examples, the previously acquired data and pre-stored data may again be data which is known or assumed to be reliable for the purpose of determining the particular physiological parameter of interest.

In any example, the previously acquired data and the pre-stored data may be previously acquired data representative of substantially the same anatomical region or feature as the newly acquired data being tested.

In each of the above examples, reference to data is reference to ultrasound data, i.e. generated by an ultrasound transducer unit.

The above examples are based on direct comparison of derived ultrasound data with previously acquired data or pre-stored data. In other examples, the testing procedure may be based on comparison of information derived from ultrasound data. Information derived from ultrasound data may refer to any information, data, measurement, or result deriving from the ultrasound data.

In particular, it may include in certain examples a physiological parameter measurement derived from ultrasound data.

It may alternatively include one or more images derived from the data. It may include one or more physiological parameter measurements derived from one or more images, where the images are derived from the ultrasound data.

The above described example procedures for determining reliability measures and applying reliability criterions, based on comparison with previously acquire data or pre-stored data may be applied in exactly analogous fashion with respect instead to information derived from the ultrasound data in each case.

For instance, the testing procedure may be based on determining a measure of similarity between results of one or more physiological parameter measurements derived from newly acquired data and measurements of the same physiological parameter derived from previously acquired data or pre-stored data.

Various examples for the testing procedure are based on making reference to previously acquired data or information derived therefrom. The previously acquired data may be data acquired by the ultrasound control unit with the ultrasound transducer unit configured in a different drive setting to that being tested, or in a plurality of different drive settings (leading to a plurality of subsets of previously acquired data for example).

The previously acquired data may include at least data acquired in the first drive setting. For example, the measure of reliability derived by the analysis unit may in some examples be based at least on a similarity of acquired ultrasound data, or information derived therefrom, of the second drive setting with corresponding data or information derived therefrom of the first drive setting.

Various examples discussed above and below include determining a measure of similarity between two sets of ultrasound data or between physiological parameters, images or other information derived therefrom.

The similarity measure may be based on performing a correlation test, for instance a correlation test between respective acquired ultrasound data signals, or information derived therefrom.

For example, for one dimensional imaging (e.g. A-line or M-mode imaging) the similarity measure may be based on performing a correlation test between respective acquired A-lines, for instance one A-line in the data to be tested and another acquired from the previously acquired data. The A-lines should be representative of substantially the same line through the body.

For two dimensional imaging for example, a correlation test may be performed between either raw data signals, or between 2D frames of a particular anatomical region of interest generated from acquired ultrasound data.

For three dimensional imaging for example, again a correlation test may be performed between raw data signals, or between 3D volumetric images of particular anatomical regions of interest generated from the ultrasound data.

For a correlation test between 2D or 3D image data, the comparison may be made based on comparison of image features. For instance, for 3D image data, the comparison may be performed between voxel intensity gradients.

For example, in some imaging methods, generated 3D images are mapped onto 3D anatomical models of the imaged region to improve the 3D representation of the data. This is based on segmentation of the acquired 3D image data, and subsequent mapping to the model.

By way of one example, first image data may be mapped to an anatomical model of the heart, the first ultrasound image data acquired using a first drive setting. The data is typically segmented and mapped based on identifying image intensity gradients (changes in image intensity, e.g. as data moves between the ventricular myocardium and a volume of blood). Therefore, there typically exists an image gradient across a model boundary. A correlation test between two data sets may be based on determining a change in such an intensity gradient in 3D images generated from the data. The reliability condition may therefore be a particular threshold change in this gradient. When the gradient reaches the critical threshold, this may be an indicator for loss of contrast, i.e. suboptimal image quality.

According to an advantageous set of embodiments, the adjustment procedure comprises acquiring multiple sample datasets in different respective drive settings (each having a different known associated power level), and wherein the reliability testing procedure is based on comparison between the multiple acquired datasets. These multiple datasets may make up the previously acquired data referred to above.

In one set of examples of this general approach, a step-wise adjustment procedure is performed. This will be discussed in more detail below.

The multiple datasets in different drive settings may be acquired at high frequency (high frame rate). For example, the multiple datasets may be acquired at a frame rate of at least 50 Hz. By acquiring at high frame rate, it can be more reliably assumed that the anatomy being captured has not substantially changed between any two frames and thus any loss in parameter quantification accuracy may be assumed due to loss of signal quality.

For example, for one-dimensional imaging, this type of imaging (e.g. A-line or m-mode) may be used to acquire multiple data subsets in very rapid succession, (for example with a frame rate >10 kHz). A correlation test may be performed between one of these acquired subsets and one or more previous of the acquired subsets to test reliability of the data for instance. If combined with anatomical intelligence available from a recent cardiac segmentation, the assessment may be further improved.

Multiple datasets can also be acquired in rapid succession using 2D imaging. For 2D imaging, high frame rate may be achieved even in reduced power by for example reducing the dimensions of the particular field of view which is imaged, or alternatively by selecting a field of view which is more spatially proximal the transducer unit (so long as such regions are suitable for deriving the particular physiological parameter of interest).

A correlation test may be performed between acquired data or images generated from the data in one drive setting and this compared with data or images acquired or generated in one or more of the other drive settings.

Multiple datasets can also be acquired in rapid succession using 3D imaging and comparison tests then performed.

In any of these examples, and as discussed above, the comparison test between one drive setting and one or more of the other settings may be based on comparison of the data or images derived from the data, or may be based on comparison for instance of the target physiological parameter (e.g. ventricular output) derived from data acquired in the different settings.

For example, the testing procedure may comprise testing whether a change in the measured physiological parameter between a first and second drive setting in the succession of settings, the second having a lower power level, has changed by some threshold amount. As noted above, the threshold may be set based on a known typical fluctuation between physiological parameter measurements acquired without changing the drive setting. This may be calculated for instance from previous measurements (if available), or may be pre-determined and pre-stored.

As discussed above, there are different approaches for determining a candidate new lower power drive setting for the transducer unit, and/or determining an optimum lower power setting for the transducer unit.

Some example approaches will now be outlined.

There was discussed above an example general approach in which multiple datasets are acquired in different respective drive settings and data from one or more of these compared with that of one or more others. One example of this approach comprises a step-wise adjustment procedure.

Hence, according to an advantageous set of embodiments, the adjustment of the drive setting may comprise a stepwise adjustment between the first and second settings, comprising stepping through successive drive setting steps of differing power levels.

Advantageously, at least a portion of the successive drive settings may have successively lower associated power levels.

For example, sample ultrasound data may be acquired by the acquisition unit in each successive drive setting, and a reliability of the sample data tested by the data analysis module. The step-wise adjustment through successively lower power level settings may then be continued until a drive setting is reached which fails to meet said pre-defined reliability condition. The second drive setting for finally adjusting the transducer unit to may then be selected as the last of the successive drive settings which met the reliability condition (i.e. the penultimate setting in the series).

The measure of reliability of each successive drive setting may be based on a determined measure of similarity of acquired ultrasound data, or information derived therefrom, with data or information derived therefrom of one or more preceding setting steps.

The reliability condition may comprise a minimum threshold for said measure of similarity for example.

According to certain examples, the measure of reliability may be based on a similarity only with data or measurements of the immediately preceding setting step.

According to one set of examples, an iterative step-wise approach may be applied for converging toward an optimally low power setting which meets the reliability condition. The stepwise adjustment may include stepping through at least a first series of successively lower power level settings, and may further include higher or lower power level settings for converging toward an ideal setting.

Figure 2:
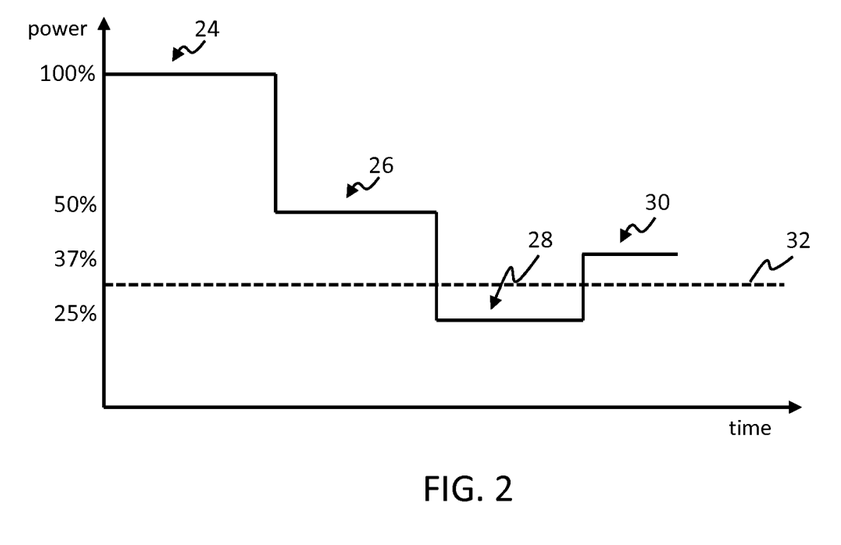
FIG. 2 illustrates a step-wise drive setting adjustment procedure as implemented according to one or more embodiments.

An example of such a stepwise adjustment approach is illustrated schematically by the graph shown in FIG. 2. The y-axis indicates a relative power level of each drive setting, and the x-axis represents time.

In this example, the adjustment procedure performed by the acquisition module starts with a first drive setting 34 having a nominal relative power of 100%. Sample data is acquired with the ultrasound transducer unit configured in this setting.

A new candidate drive setting 26 is then provisionally switched to having half the power of the first setting. Sample ultrasound data is then acquired in this setting. This data, or information (e.g. a physiological parameter or image) derived from this data is then compared with that of the preceding setting 24, and a similarity measure derived. The testing module determines whether the similarity measure is within a pre-defined similarity threshold (this being the applied reliability condition).

If the similarity does fall within the defined threshold, then a new candidate drive setting 28 is then provisionally switched to, again having half the power of the preceding 26 setting. Sample ultrasound data is again acquired in this new setting and the data, or information derived therefrom compared to that of the preceding setting 26. In this illustrative example, this new setting 28 is assumed to have fallen below a minimum level of reliability for deriving the particular physiological parameter of interest. The de facto minimum power level is indicated schematically by the dotted horizontal line 32.

Responsive to a determination by the analysis module 16 that the data does not meet the pre-defined reliability condition (the pre-defined similarity threshold in this case), a next new candidate drive setting 30 is provisionally switched to, this one having 50% greater power than the preceding 28 setting.

Sample data is again acquired in this new drive setting 30, and this is tested by the analysis module 16 to determine whether it meets the reliability condition. The sample data or information derived therefrom may be compared for example with data or information derived using the last setting in the series whose data was known to have satisfied the reliability condition, i.e. in this example drive setting 26.

In some examples, in the case the new, higher power, drive setting 30 meets the pre-defined reliability condition, this candidate setting 30 may be selected as the second drive setting and the ultrasound transducer unit 12 maintained or indefinitely switched to this drive setting. In other examples, the iterative adjustment might continue in similar fashion, to converge closer to a de facto minimum possible power level setting 32 which still passes the reliability condition. A set maximum further number of iterations may be defined, and the procedure continued until these are completed.

To ensure that data acquired in each step represents substantially the same anatomical picture, each set of sample data (acquired in each different drive setting) may be controlled to be acquired at the same point in a given cardiac cycle (where the physiological parameter is a cardiac parameter). This ensures that any deviation in data may be substantially attributed to loss of data quality due to reducing the power, rather than changes in anatomy.

For example, sample data in the different drive settings may be gated by an input ECG sensor signal, the ECG sensor coupled to the subject being monitored. Sample data acquired in each drive setting may be gated, i.e. pegged, to the same point in the cardiac phase, e.g. end-systole or end-diastole. Ultrasound data is then acquired at the same phase in the cardiac cycle based on morphological analysis of the ECG wave acquired from the patient. One example of this might be gating data acquisitions at the peak of the R-wave.

An alternative approach to ensuring anatomical equivalence between data acquired in different drive settings is to step through the different candidate drive settings at high frequency, e.g. a frame rate of at least 50 Hz, with sample data being acquired in each setting. By stepping through at high frequency, collected datasets in the different drive settings have only a small time delay between them, meaning anatomy has not substantially changed between the two.

Figure 3:
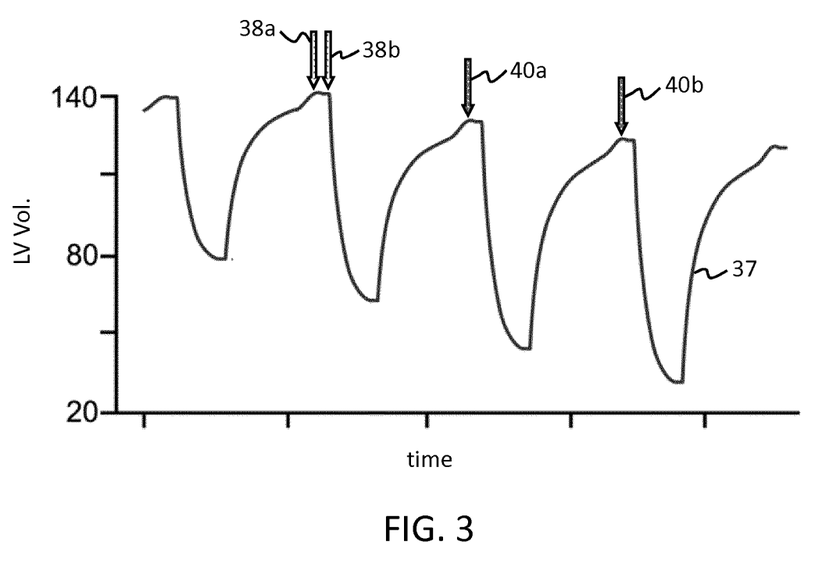
FIG. 3 illustrates example timing options for data acquisition in successive drive setting steps.

FIG. 3 schematically illustrates these two approaches. The x-axis shows time. The y-axis represents left ventricle volume of an example subject. The waveform 37 represents an ECG signal progressing through various cardiac phases.

Arrows 38*a*, 38*b* respectively represent timings of acquisition of ultrasound data in two successive drive setting steps. In this case, the settings are progressed through at high frequency, meaning there is little time delay between the two. Both are performed at the same end diastole phase.

Arrows 40*a*, 40*b* represent timings of acquisition of ultrasound data in two example successive drive settings. In this case, acquisition of sample data in the successive drive settings is ECG-gated, in this example gated to end-diastole. Each acquisition again occurs at the same point in the cardiac phase, but with some time delay between them. The anatomy should still however be substantially similar.

Figure 4:
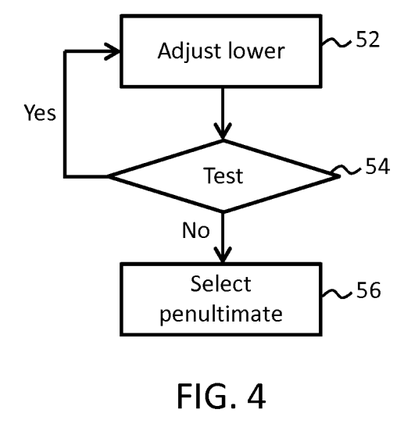
FIG. 4 illustrates an example method for adjusting a drive setting of a transducer unit, using a step-wise adjustment approach.

An example method for adjusting a drive setting of an ultrasound transducer unit according to one or more embodiments is shown in block diagram form in FIG. 4. This example method is based on a step-wise adjustment approach.

The method comprises provisionally adjusting 52 a transducer unit from an initial first drive setting to a first candidate drive setting, having a known lower power level than the first initial setting. Sample ultrasound data is then acquired in this candidate drive setting and this is tested 54 in accordance with a testing procedure, as outlined in any of the examples or embodiments described above. This involves deriving a measure of reliability of the acquired data for determining one or more physiological parameters, and determining whether this reliability meets a pre-defined reliability condition.

For example, the acquired data or information derived therefrom (e.g. a physiological parameter derived from the data or an image generated from the data) may be compared with data acquired in the initial drive setting and a similarity measure derived. The reliability condition may be a defined minimum threshold for this similarity measure.

If the reliability condition is met, the method then loops back to the first step 52 and the transducer unit 12 is again provisionally switched to a new candidate drive setting of again lower power than the preceding setting. Ultrasound data is acquired in this new drive setting and again tested 54 with the testing procedure as described in examples above to determine whether the data meets the pre-defined reliability condition.

The method continues step-wise in this way until a candidate drive setting is reached which does not meet the defined reliability condition. At this point, the last drive setting in the step-wise series which did pass the pre-defined reliability condition is selected 56 as the new final drive setting for the transducer unit 12 and the transducer unit is switched indefinitely to this drive setting. In practice, this will be the penultimate drive setting in the step-wise series of candidate drive settings (i.e. the setting immediately preceding the setting which failed the reliability condition).

Figure 5:
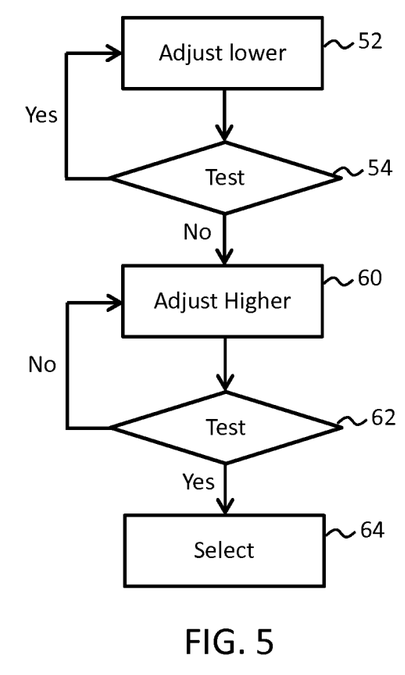
FIG. 5 illustrates a further example method for adjusting a drive setting of a transducer unit, using a variant step-wise adjustment approach.

A further example method for adjusting a drive setting of an ultrasound transducer unit according to one or more embodiments is shown in block diagram form in FIG. 5. This example method is again based on a step-wise iterative adjustment approach. This method is similar to that described in relation to FIG. 2 above.

The method is the same as the method of FIG. 4 for the first few steps. In particular, the method comprises first provisionally adjusting 52 the transducer unit 12 from an initial first drive setting to a first candidate drive setting, having a known lower power level than the first initial setting. For example, the new candidate drive setting may have a power level 50% lower than the preceding setting. Sample ultrasound data is then acquired and tested 54 in accordance with the testing procedure, as outlined in any of the examples above.

For example, the acquired data or information derived therefrom may be compared with data acquired in the preceding drive setting and a similarity measure derived. The reliability condition may be a defined minimum threshold for this similarity measure.

If the reliability condition is met, the method then again loops back to the first step 52 and the transducer unit 12 is again provisionally switched to a new candidate drive setting of again lower power than the preceding setting. Ultrasound data is acquired in this new drive setting and again tested 54 with the testing procedure as described in examples above to determine whether the data meets the pre-defined reliability condition.

The method continues step-wise in this way until a candidate drive setting is reached which does not meet the defined reliability condition.

At this point, the method comprises provisionally adjusting 60 the transducer unit to a new candidate drive setting, this one having a known higher power level than the last. For example, the new candidate drive setting may have a power level 50% higher than the preceding setting.

Sample data is then again acquired in this new higher setting and this then tested 62 for reliability in accordance with any example testing procedure described above.

If the data of this new higher setting meets the reliability condition, then this new higher setting is selected as the final drive setting for indefinitely adjusting the transducer unit to. If the data still fails the reliability condition, the method loops back and a new candidate drive setting is again moved to, again having a higher power level than the preceding step, for example 50% higher power level. Data in this new candidate drive setting is again tested 62 to see if it meets the minimum reliability condition.

This is continued until a candidate drive setting is reached which meets the reliability condition. This is then selected as the final drive setting for adjusting the transducer unit to on an on-going or final basis.

Various further advantageous options and variations for an example ultrasound control unit, or example control method, according to one or more embodiments will now be outlined. These options may be applied or combined with any of the example embodiments discussed above for example.

According to an advantageous set of embodiments, the control unit (or method) is further configured with an override mode, in which the drive setting is automatically switched to a pre-defined high power drive setting in the event a pre-defined override condition is met.

The override condition may be based on properties of acquired ultrasound data and/or inputs of one or more external sensors or devices operatively coupled to the system.

Here, certain contextual information about a monitored patient is monitored and certain changes in this information can be used to trigger override of the power saving settings, and switching automatically to a higher power setting, for example a pre-defined full power or "high power" mode.

The override condition may be based on a particular value of one or more auxiliary properties or parameters being met, for instance a particular threshold of one or more parameters being met. It may additionally or alternatively be time based, for instance triggered by elapsing of a certain (e.g. regular) interval of time. By way of example, the override condition for triggering the override mode may include one or more of the following factors.

A threshold level of one or more physiological parameters of vital signs, such as $SpO_2$, heart rate, ECG (e.g. heart rate variability changes by 10%).

Detected movement of the ultrasound transducer unit relative to the subject body, for example based on an input from an accelerometer or other motion sensor, or electronic motion sensing, based on analysis of ultrasound data.

Detected presence of a caregiver (e.g. with a movement or proximity sensor, or through detecting touch of a control panel or of the ultrasound transducer unit for instance. The system may in this case be temporarily adjusted to the pre-defined high power mode to generate better images for interpretation. This may be for a pre-defined time temporary time period for instance, before switching back to a power saving mode.

Detection of an urgent change in medical condition or status, e.g. a change which triggers an alarm on an associated patient monitor unit. Here, switching to high power mode permits checking with greater accuracy or precision data whether the condition of the patient really is critical.

Detection of passing of a defined period or interval of time. For example, the high power setting may be temporarily switched to recurrently at regular intervals, e.g. every 30 minutes.

According to any embodiment of the invention, the ultrasound control unit 10 may be operable, in addition to the power adjustment functionality described above and below, to control the ultrasound transducer unit to acquire ultrasound data and to monitor one or more physiological parameters based on that ultrasound data.

Deriving physiological parameters based on acquired ultrasound data is based on processing the data, or images derived from the data, with a particular algorithm or procedure. Different specific parameter extraction algorithms and procedures exist, depending upon the parameter to be extracted and the type and appearance of images or data which is used as input. Most extraction methods are based on generating an image from acquired ultrasound data and applying image segmentation to derive dimensions for instance of key anatomical features.

According to one or more embodiments, the applied extraction method may be adjusted in dependence upon the particular drive setting in which the transducer unit is configured, for instance in dependence upon the power level of the particular drive setting.

For example, if the appearance of images derived from data of different drive settings is different, e.g. due to lowering of resolution caused by lower power, a different extraction method for the physiological parameter may be better suited and provide more accurate results For the model-based segmentation for example, algorithms for boundary detection may be adjusted in dependence upon the drive setting of the transducer unit.

According to one or more embodiments, the control unit (or method) may be configured with a low battery mode. In cases where the ultrasound transducer unit is powered by a battery or other local power source, the control unit may be adapted to monitor the power level of the power source and detect when a power level of the power source falls below a pre-defined threshold. Responsive to this, the control module of the control unit may be adapted, using the acquisition unit, to switch to a new drive setting having a further reduced power level.

The analysis unit may be adapted to apply a different testing procedure, for instance having a lower allowable measure of reliability for the reliability condition. This allows the power of the transducer level to be reduced to a critically low level (to avoid total failure due to power exhaustion), but at the cost of some further accuracy in measured physiological parameters. Monitoring time is thereby extended.

In accordance with one or more embodiments, the ultrasound control unit 10 (or method) may be configured with a 'cool-down' mode, in which the transducer unit is temporality deactivated, responsive to detection of a maximum threshold temperature of the transducer unit being exceeded. There may be a temperature sensor provided for this purpose, arranged sensing a temperature at the transducer unit.

In advantageous examples, the control unit is adapted to monitor an output of the temperature sensor and detect exceeding of a first warning threshold for the temperature and further detect exceeding of a further (higher) critical threshold for the temperature. The first warning threshold may be characterized by a particular threshold temperature level in combination with a positive temperature gradient with time.

On passing of the warning threshold, the control unit may be adapted to monitor a status of the patient, and to trigger said temporary cool-down mode responsive to detecting a status of the patient is in a pre-defined safe state.

In this way, it can be ensured that cool-down is triggered to avoid critical overheating, but that it is proactively triggered in advance of overheating (at a warning threshold), timed to coincide with a safe time/phase, based on the patient condition.

There are listed below some examples of indicators which might be used to indicate a safe state of the patient for triggering the cool down mode.

Levels of vital signs, e.g. monitored by one or more auxiliary physiological sensors, are detected to have remained stable for a pre-defined threshold time period. The one or more physiological parameters being monitored using acquired ultrasound data (e.g. left ventricle volume, stroke volume, cardiac output) have remained stable for a pre-defined minimum time period.

Occurrence of a particular period of the cardiac cycle, detected for instance based on ECG signals. For example, the control unit may be adapted to recurrently enter the transducer unit into cool-down mode during certain portions of the cardiac cycle and then to return it to active mode during other portions of the cardiac cycle. In this way, intelligent power saving is achieved by only having the ultrasound transducer unit active during cardiac relevant phase periods.

Preferably, the control unit is adapted to detect reduction of the temperature back below the warning temperature threshold, and responsive to this adapted to deactivate the cool-down mode and return the ultrasound transducer unit to active mode. This may comprise first returning the ultrasound transducer unit to full power mode, before subsequently performing drive setting adjustment to reduce power to a lower power level setting, in accordance with any of the examples or embodiments outlined above.

According to advantageous examples, the ultrasound control unit 10 may be, further operably coupleable with a patient monitoring system. The ultrasound control unit may for instance include a connection output for operatively coupling with a patient monitoring unit. In some examples, the ultrasound control unit may be adapted to couple in modular fashion with a monitoring unit of a patient monitoring system. For instance, the control unit may be configured as an expansion block for receipt within a co-operating slot of a patient monitoring unit.

Examples in accordance with a further aspect of the invention provide an ultrasound system, comprising:
   an ultrasound transducer unit 12 operable to acquire ultrasound data; and
   an ultrasound control unit 10 in accordance with any of the examples or embodiments described above or below, or in accordance with any claim of this application, operatively coupled with the ultrasound transducer unit.

Examples in accordance with a further aspect of the invention provide a patient monitoring system comprising:
   a patient monitoring unit; and
   an ultrasound control unit in accordance with any of the examples or embodiments described above or below, or in accordance with any claim of this application.

The patient monitoring unit may be coupleable or coupled with one or more physiological parameter (e.g. vital sign) measurement or monitoring devices. The patient monitoring unit may include a display.

The ultrasound control unit may be adapted, in addition to the power adjustment functionality described above, to control the ultrasound transducer unit to acquire ultrasound data and to monitor one or more physiological parameters based on that ultrasound data.

Alternatively the ultrasound system may comprise a further unit configured to control the ultrasound transducer unit to acquire ultrasound data and to derive one or more physiological parameters based on that data.

Figure 6:
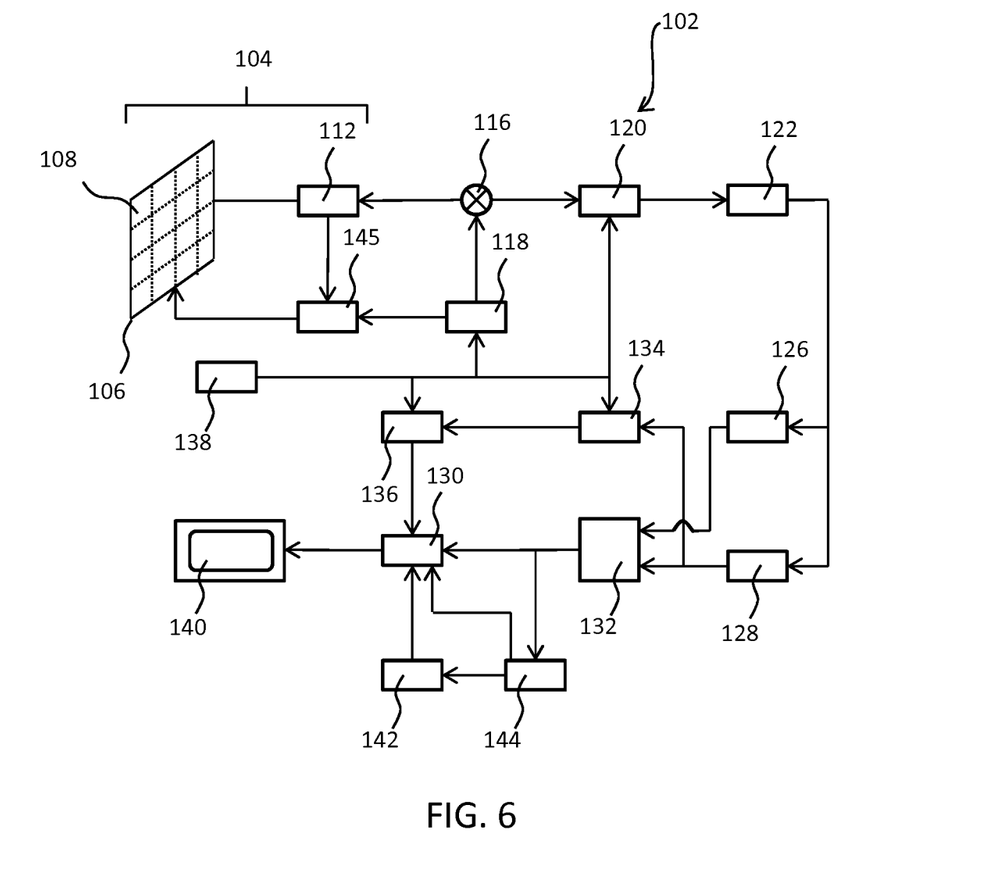
FIG. 6 illustrates an example ultrasound system according to one or more embodiments.

The general operation of an exemplary ultrasound system will first be described, with reference to FIG. 6. The various components of the exemplary ultrasound system described below may for instance be comprised by an overarching control unit or monitoring unit coupled to the ultrasound control unit of the present invention, or may be distributed between different units, or may be included in the ultrasound control unit according to the invention.

The system comprises an ultrasound transducer unit in the form of an array transducer probe 104. The array transducer probe has a transducer array 106 for transmitting ultrasound waves and receiving echo information. The transducer array 106 may comprise CMUT transducers; piezoelectric transducers, formed of materials such as PZT or PVDF; or any other suitable transducer technology. In this example, the transducer array 106 is a two-dimensional array of transducers 108 capable of scanning either a 2D plane or a three dimensional volume of a region of interest. In another example, the transducer array may be a 1D array.

The transducer array 106 is coupled to a microbeamformer 112 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 116, which the microbeamformer 112 can be coupled to and which switches the array between transmission and reception modes, and protects the main beamformer 120 from high energy transmit signals in the case where a microbeamformer is not used and the transducer array is operated directly by the main system beamformer. The transmission of ultrasound beams from the transducer array 106 is directed by a transducer controller 118 coupled to the microbeamformer by the T/R switch 116 and a main transmission beamformer (not shown), which can receive input from the user's operation of the user interface or control panel 138. The controller 118 can include transmission circuitry arranged to drive the transducer elements of the array 106 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 118 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 118 can be coupled to control a DC bias control 145 for the transducer array. The DC bias control 145 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 112 and are then passed to a main receive beamformer 120 where the partially beamformed signals from individual patches of transducers are combined into a fully beamformed signal, referred to as radio frequency (RF) data. The beamforming performed at each stage may be carried out as described above, or may include additional functions. For example, the main beamformer 120 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 122. The signal processor 122 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 6 only the receiver beamformers 112, 120 are shown, for simplicity. In the complete system, there will also be a transmission chain with a transmission micro beamformer, and a main transmission beamformer.

The function of the micro beamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 106 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 126 and a Doppler processor 128. The B mode processor 126 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 128 processes temporally distinct signals arising from tissue movement and blood flow for the detection of moving substances, such as the flow of blood cells in the image field. The Doppler processor 128 typically includes a wall filter with parameters set to pass or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 140. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for display on an image display 140. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow in addition to structural measurements such as the sizes of organs and gestational age. The quantification processor may receive input from the user control panel 138, such as the point in the anatomy of an image where a measurement is to be made.

Output data from the quantification processor is coupled to a graphics processor 136 for the reproduction of measurement graphics and values with the image on the display 140, and for audio output from the display device 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 138, such as patient name. The user interface is also coupled to the transmit controller 118 to control the generation of ultrasound signals from the transducer array 106 and hence the images produced by the transducer array and the ultrasound system. The transmit control function of the controller 118 is only one of the functions performed. The controller 118 also takes account of the mode of operation (given by the user) and the corresponding required transmitter configuration and bandpass configuration in the receiver analog to digital converter. The controller 118 can be a state machine with fixed states.

The user interface is also coupled to the multi-planar reformatter 144 for selection and control of the planes of multiple multi-planar reformatted (MPR) images which may be used to perform quantified measures in the image field of the MPR images.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ultrasound control unit, operably coupleable with an ultrasound transducer, the ultrasound control unit comprising: one or more processors configured to:
control acquisition of ultrasound data using the ultrasound transducer;
control a drive setting of the ultrasound transducer, each possible drive setting having a known or derivable transducer power level processor;
perform a testing procedure based on acquired ultrasound data, to determine a measure of reliability of the data for deriving one or more physiological parameters, and to determine whether said reliability measure meets a defined reliability condition; and
adjust a drive setting of the ultrasound transducer from a first setting to a second, lower power, setting, wherein the second setting meets said defined reliability condition.

2. The ultrasound control unit as claimed in claim 1, wherein the second drive setting is selected to be a minimum available power level setting which meets the defined reliability condition.

3. The ultrasound control unit as claimed in claim 1, wherein the testing procedure is based on reference to previously acquired, or pre-stored, ultrasound data or information derived therefrom.

4. The ultrasound control unit as claimed in claim 3, wherein the measure of reliability is based on a determined measure of similarity of acquired ultrasound data, or information derived therefrom, with said previously acquired, or pre-stored, data or information derived therefrom.

5. The ultrasound control unit as claimed in claim 4, wherein the measure of reliability is based at least on a measure of similarity of acquired ultrasound data, or information derived therefrom, of the second drive setting with corresponding data or information derived therefrom of the first drive setting.

6. The ultrasound control unit, as claimed in claim 4, wherein the measure of reliability is based on a measure of similarity with previously acquired data, or information derived therefrom, the previously acquired data having been acquired within a defined time period of the data being tested, and the reliability condition being a minimum threshold for said measure of similarity.

7. The ultrasound control unit as claimed in claim 6, wherein said minimum similarity threshold is set based on a pre-stored or derived average measure of similarity between previously acquired, or pre-stored, data subsets, or information derived therefrom, said previous data subsets also acquired within said defined time period of one another.

8. The ultrasound control unit as claimed in claim 1, wherein the testing procedure is based on deriving one or more ultrasound images from acquired data and wherein the measure of reliability is based on a similarity of one or more characteristics of the derived image(s) with corresponding characteristics of image(s) derived from previously acquired or pre-stored data.

9. The ultrasound control unit as claimed in claim 1, wherein the adjustment of the drive setting comprises a stepwise adjustment between the first and second settings, comprising stepping through successive drive setting steps of differing power levels.

10. The ultrasound control unit as claimed in claim 9, wherein at least a portion of the successive drive settings have successively lower associated power levels.

11. The ultrasound control unit as claimed in claim 9, wherein sample ultrasound data is acquired in each successive drive setting, and a reliability of the sample data tested by the data analysis module, and wherein the step-wise adjustment is continued until a drive setting is reached which fails to meet said pre-defined reliability condition.

12. The ultrasound control unit as claimed in claim 9, wherein
sample ultrasound data is acquired in each successive drive setting step, and
determine the reliability of each successive drive setting is based on a determined measure of similarity of acquired ultrasound data, or information derived therefrom, with data or information derived therefrom of one or more preceding settings.

13. The ultrasound control unit as claimed in claim 9, wherein sample ultrasound data is acquired in each successive drive setting step, and wherein the steps are advanced through at a step rate of at least 1 step per second.

14. The ultrasound control unit as claimed in claim 1, wherein the control unit is further configured with an override mode, in which the ultrasound transducer is automatically switched to a pre-defined high power drive setting in the event a pre-defined override condition is met, and optionally wherein the override condition is based on properties of acquired ultrasound data and/or inputs of one or more external sensors or devices operatively coupled to the system.

15. An ultrasound system, comprising:
   an ultrasound transducer unit operable to acquire ultrasound data; and
   an ultrasound control unit as claimed in claim 1, operatively coupled with the ultrasound transducer unit.

16. A patient monitoring system comprising:
   a patient monitoring unit; and
   an ultrasound control unit as claimed in claim 1.

* * * * *